United States Patent [19]
Levy

[11] Patent Number: 6,068,972
[45] Date of Patent: May 30, 2000

[54] METHODS AND COMPOSITIONS FOR REDUCING BACTERIAL TOLERANCE TO ANTIBACTERIALS, DISINFECTANTS AND ORGANIC SOLVENTS

[75] Inventor: Stuart B. Levy, Boston, Mass.

[73] Assignee: Trustees of Tufts College, Medford, Mass.

[21] Appl. No.: 08/946,225

[22] Filed: Oct. 7, 1997

Related U.S. Application Data

[60] Provisional application No. 60/060,898, Oct. 3, 1997.

[51] Int. Cl.$^7$ .............................. C12Q 1/68; G01N 33/53
[52] U.S. Cl. ................................. 435/4; 435/6; 435/7.1; 435/69.1; 536/23.1
[58] Field of Search ............................... 435/6, 7.1, 61.1, 435/91.31; 536/23.1, 23.2, 24.5

[56] References Cited

U.S. PATENT DOCUMENTS

| | | | |
|---|---|---|---|
| 5,384,259 | 1/1995 | Rothstein et al. | 803/635 |
| 5,817,793 | 10/1998 | Levy | 536/23.1 |

FOREIGN PATENT DOCUMENTS

| | | |
|---|---|---|
| 0 547 403 A1 | 6/1993 | European Pat. Off. . |
| 0 548 557 A1 | 6/1993 | European Pat. Off. . |
| WO 96/33285 | 10/1996 | WIPO . |

OTHER PUBLICATIONS

Miller et al "Overlaps and Parallels in the Regulation of Intrinsic Multiple–Antibiotic Resistance in *Eschericia coli*" Molecular Microbiology vol. 21(3):441–448, 1996.
Miller et al. "Genetic Relationships Between soxRS and mar Loci in Promoting Multiple Antibiotic Resistance in *Eschericia coli*" Antimicrobial Agents and Chemotherapy vol. 38(8):1773–1779, 1994.
Aono, Rikizo et al. (1995) "A Close correlation Between Impovement of Organic Solvent Tolerance Levels And Alteration of Resistance Toward Low Levels of Multiple Antibiotics in *Escherichia Coli*" Biosci. Biotech. Biochem. vol. 59, No. 2, pp. 213–218.
Ariza Rafael R. et al. (1995) "Activation of Multiple Antibiotic Resistance and Binding of Stress–Inducible Promoters by *Escherichia coli* Rob Protein", Journal of Bacteriology vol. 177, No. 7, pp. 1655–1661.
Cohen, Seth P. et al. (1989) "Cross–Resistance to Fluoroquinolones in Multiple–Antibiotic–Resistant (Mar) *Escherichia coli* Selected by Tetracycline or Chloramphenicol: Decreased Drug Accumulation Associated with Membrane Changes in Addition to OmpF Reduction" Antimicrobial Agents and Chemotherapy vol. 33, No. 8, pp. 1318–1325.
Cohen, Seth P. et al. (1993) "Salicylate Induction of Antibiotic Resistance in *Escherichia coli*: Activation of the mar Operon and a mar–Independent Pathway" Journal of Bacteriology vol. 175, No. 24, pp. 7856–7862.
George, Anthony M. et al. (1983) "Amplifiable Resistance to Tetracycline, Chloramphenicol, and Other Antibiotics in *Escherichia coli*: Involvement of a Non–Plasmid–Determined Efflux of Tetracycline" Journal of Bacteriology Journal of Bacteriology vol. 155, No. 2 pp. 531–540.

Goldman, John et al. (1996) "A Central Role For The Multiple Antibiotic Resistance (mar) Locus in *E. Coli* in Organic Solvent Tolerance" AMS General Meeting.
Lewis, Kim "Multidrug Resistance Pumps In Bacteria; Variations on a Theme" (1994) TIBS 19 Reviews pp. 119–123.
Lewis, Kim et al. "Multidrug Resistance Pumps provide Broad Defense" ASM News vol. 63, No. 11 pp. 605–610; 1996.
Ma, Dzwokai et al. (1996) "The Local Repressor AcrR Plays A Modulating Role In The Regulation of acrAB Genes of *Escherichia Coli* by Global Stress Signals" Molecular Microbiology vol. 19, No. 1 pp. 101–112.
McMurry, Laura M. et al. (1994) "Active Efflux of Chloramphenicol in Susceptible *Escherichia coli* Strains and in Multiple–Antibiotic–Resistant (Mar) Mutants" Antimicrobial Agents and Chemotherapy vol. 38, No. 3, pp. 542–546.
Nakajima, Harushi et al. (1995) "soxRS Gene Increased The Level of Organic Solvent Tolerance In *Escherichia Coli*" Biosci. Biotech. Bicochem. vol. 5, No. 7 pp. 1323–1325.
Nakajima, Harushi et al. (1995) "Overexpression of the robA Gene Increases Organic Solvent Tolerance and Multiple Antibiotic and Heavy metal Ion Resistance in *Escherichia colil*" Applied and Environmental Microbilogy vol. 61, No. 6, pp. 2302–2307.
Nikaido, Hiroshi (1996) "Multidrug Efflux Pumps of Gram–Negative Bacteria" Journal of Bacteriology, vol. 178, No. 20 pp. 5853–5859.
Okusu, Haruko et al. (1996) "AcrAB Efflux Pump Plays a Major Role in the Antibiotic Resistance Phenotype of *Escherichia coli* Multiple–Antibiotic–Resistance (Mar) Mutants" Journal of Bacterilogy vol. 178, No. 1 pp. 306–308.
Paulsen, Ian et al. (1996) "Protein–Dependent Multidrug Efflux Systems" vol. 60, No. 4, pp. 575–608.
White, David G. et al. (1997) "Role of the acrAB Locus in Organic Solvent Tolerance Mediated by Expression of marA, soxS, or robA in *Escherichia coli*" Journal of Bacteriology, vol. 179, No. 19, pp. 6122–6126.

*Primary Examiner*—John S. Brusca
*Assistant Examiner*—Sean M Garry
*Attorney, Agent, or Firm*—Lahive & Cockfield, LLP; Elizabeth A. Hanley, Esq.; Megan E. Williams

[57] ABSTRACT

The invention relates to methods and compositions for manipulating bacterial resistance to non-antibiotic antibacterial compositions, disinfectants and organic solvents. The invention provides methods for rendering bacterial cells susceptible to non-antibiotic antibacterial compositions. Also provided are methods to reduce the selection of bacterial mutants having an multiple antibiotic resistance phenotype by non-antibiotic antibacterial compositions. The invention also provides methods for testing the ability of non-antibiotic antibacterial compositions to select for or induce a multiple antibiotic resistance phenotype in bacteria. Also provided are methods for increasing or decreasing bacterial tolerance to organic solvents by increasing or decreasing the activity of bacterial organic solvent efflux pumps. Compositions useful in the foregoing methods are also provided.

6 Claims, 1 Drawing Sheet

METHODS AND COMPOSITIONS FOR REDUCING BACTERIAL TOLERANCE TO ANTIBACTERIALS, DISINFECTANTS AND ORGANIC SOLVENTS

RELATED APPLICATIONS

This application claims benefit of U.S. provisional application Ser. No. 60/060,898, filed Oct. 3, 1997.

GOVERNMENT SUPPORT

This work was supported in part by U.S. Public Health Service grant number GM51661. The government may have certain rights in this invention.

FIELD OF THE INVENTION

This invention relates to methods and compositions for manipulating bacterial resistance to non-antibiotic antibacterial compositions, disinfectants and organic solvents.

BACKGROUND OF THE INVENTION

Antibiotic or antimicrobial substances have long been used to inhibit the growth of bacteria or other microbes and to treat bacterial or microbial infections in humans, other animals, and in tissue culture. The use of antibiotics or antimicrobials in a treatment regimen, however, has the undesirable effect of selecting for bacteria or other microbes which are resistant to those antibiotics or antimicrobials which are administered or applied. As a result, treatment regimens can be adversely affected or, in some cases, rendered ineffective. This necessitates a continual search for new antibiotics and antimicrobials.

Of particular interest is the discovery of bacteria which express a multiple antibiotic resistance phenotype (Mar). This phenotype entails simultaneous resistance to a multiplicity of antibiotics which are unrelated in chemical structure. The appearance of such bacteria and infections by such bacteria greatly increase the difficulty of identifying effective antibiotics and treating infections in humans or other animals.

Multiple antibiotic resistance in bacteria is most commonly associated with the presence of plasmids and/or transposons which contain one or more resistance genes, each encoding a single antibiotic resistance phenotype. Multiple antibiotic resistance associated with the chromosome, however, has been reported in *Klebsiella, Enterobacter, Serratia* (Gutmann et al., *J. Infect. Dis.* 151:501–507, 1985), Neisseria (Johnson and Morse, *Sex. Transm. Dis.* 15:217–224, 1988), and Escherichia (George and Levy, *J. Bacteriol.*155:531–540, 1983).

Bacteria expressing a chromosomal multiple antibiotic resistance phenotype can be isolated by selecting bacteria with a single antibiotic and then screening for cross-resistance to structurally unrelated antibiotics. For example, George and Levy initially described a chromosomal multiple antibiotic resistance system which exists in *Escherichia coli* and which can be selected by a single drug, e.g., tetracycline or chloramphenicol (George and Levy, 1983). In addition to resistance to the selective agents, the Mar phenotype includes resistance to structurally unrelated agents, including nalidixic acid, rifampin, penicillins, and cephalosporins (George and Levy 1983) as well as fluoroquinolones (Cohen et al. 1989).

The chromosomal gene locus which correlates with the Mar phenotype observed in *E. coli* has been identified. The chromosomal mar locus, located at 34 min on the *E. coli* chromosomal map, is involved in the regulation of intrinsic susceptibility to structurally unrelated antibiotics (Cohen et al., *J. Bacteriol.* 175:1484–1492, 1993; Cohen et al., *Antimicrob. Agents and Chemother.* 33:1318–1325, 1989; Cohen et al., *J. Bacteriol.* 170:5416–22, 1988; Goldman et al., *Antimicrob. Agents Chemother.* 40:1266–1269, 1996), as well as the expression of antioxidant genes (Ariza et al., *J. Bacteriol.* 176:143–148, 1994; Greenberg et al.,*J. Bacteriol.* 173:4433–4439, 1991) and internal pH homeostasis (Rosner and Slonczewski, *J. Bacteriol.* 170:5416–22, 1994). The mar locus consists of two transcription units (marC and marRAB) which are divergently transcribed from a central putative operator-promotor region (marO) (Cohen et al., 1993; Goldman et al., 1996). marR is the repressor of the marRAB operon (Cohen et al., 1993; Martin and Rosner, *Proc. Natl. Acad. Sci. USA* 92:5465–5460, 1995; Seoane and Levy, *J. Bacteriol.* 177:3414–3419, 1995). Mutations in marR result in increased expression of the marRAB operon. Overexpression of marA alone is sufficient to produce the multiple antibiotic resistance phenotype (Cohen et al., 1993; Gambino et al., *J. Bacteriol.* 175:2888–2894, 1993; Yan et al., Abstr. A-26, p. 5, In Abstracts of the 1992 General Meeting of the American Society for Microbiology, American Society for Microbiology, Washington, D.C., 1992). marB has no effect of its own; however, when it is present on the same construct with marA, it produces a small increase in antibiotic resistance (White et al., Abst A-104, p. 20. In Abstracts of the 1994 General Meeting of the American Society for Microbiology, American Society for Microbiology, Washington, D.C. 1994). The function of marC is unknown; however, it also appears to enhance the multiple antibiotic resistance phenotype when cloned on the same DNA fragment with the marRAB operon (Goldman et al., 1996; White et al., 1994).

Overexpression of marA confers multiple antibiotic resistance via increased efflux of antibiotics, including fluoroquinolones, tetracycline, and chloramphenicol (Cohen et al., 1989; George and Levy, 1983; McMurry et al., *Antimicrob. Agents Chemother.* 38:542–546, 1994). Transcription of the acrAB operon, which encodes a multi-drug efflux pump whose expression is modulated by global stress signals (Ma et al., *Mol. Microbiol.* 16:45–55, 1995; Ma et al., *Mol. Microbiol.* 19:101–112, 1996), was shown to be elevated in strains containing marR mutations and displaying the Mar phenotype (Okusu et al., *J. Bacteriol.* 178:306–308, 1996). Moreover inactivation of acrAB led to increased antibiotic susceptibility in wild type and Mar mutants (Okusu et al., 1996).

More recently, mutations of marR have been found in clinical isolates resistant to quinolones (Maneewannakul and Levy, 1996). Thus mar mutants can be selected under clinical conditions and not merely under controlled laboratory conditions. Early mar mutants (i.e.,"first-step" mar mutants) remain susceptible to many common antibiotics, although such mutants can achieve levels of clinical resistance to certain antibiotics, including tetracycline, nalidixic acid and rifampin (reviewed by Alekshun and Levy, *Antimicrob. Agents Chemother.* 41:2067–2075, 1997). First-step mar mutants thus may serve as precursors of bacterial mutants which display higher levels of resistance resulting from additional mutations on the chromosome. Thus it has been demonstrated that antibiotics can select for mutations in chromosomal gene loci which confer multiple antibiotic resistance under clinical conditions.

Non-antibiotic antibacterial compositions such as disinfectants are widely used in both clinical and consumer environments for reducing bacterial contamination of work surfaces, equipment, products and the like. These non-antibiotic antibacterial compositions have been incorporated into a wide spectrum of cleansers, disinfectant compositions, soaps, lotions, plastics, etc. It is not known whether exposure of bacteria to non-antibiotic antibacterial compositions also can select for bacterial mutants, including those which display a multiple antibiotic resistance phenotype.

SUMMARY OF THE INVENTION

It has now been discovered that bacterial mutants having multiple antibiotic resistance can be selected by non-antibiotic antibacterial agents such as common disinfectants. It further has been discovered that the phenotype of the multiple antibiotic resistant mutants selected by a non-antibiotic antibacterial agent results from mutations in chromosomal gene loci which regulate expression of efflux pumps, which loci have been implicated in multiple antibiotic resistance phenotypes as described above. The efflux pumps actively pump out the non-antibiotic antibacterial agents, as well as organic solvents and antibiotics, thereby rendering the mutant bacteria resistant to all of the foregoing compounds.

According to one aspect of the invention, a method is provided for inhibiting the selection and/or propagation of a bacterial mutant that overexpresses an efflux pump. Bacteria are contacted with an agent that binds to a gene locus (the expression of the gene locus enhances expression of the efflux pump) or an expression product thereof, in an amount effective to inhibit the gene locus-enhanced expression of the efflux pump. In preferred embodiments, the gene locus is selected from the group consisting of a mar locus, a sox locus and a rob locus. Also in preferred embodiments, the efflux pump is acr-like, including the acrAB efflux pump.

The agent can be selected from the group consisting of chemicals, antisense nucleic acids, antibodies, ribozymes, and proteins which repress expression of the gene locus. A preferred embodiment is an agent that is an antisense nucleic acid, and in particularly preferred embodiments, the agent is antisense to the mar locus, sox locus and/or rob locus. Another preferred embodiment is chemical inhibitors of efflux pumps, particularly L-phenylalanyl-L-arginyl-β-naphthylamide.

According to another aspect of the invention, a method is provided for rendering bacterial cells more susceptible to a non-antibiotic bactericidal or bacteriostatic agent that is a substrate of an efflux pump. An inhibitor of a gene locus or an expression product thereof is administered to a bacterial cell, wherein the expression of the gene locus enhances expression of an efflux pump. In preferred embodiments the gene locus is selected from the group consisting of a mar locus, a sox locus and a rob locus. In other preferred embodiments the efflux pump is acr-like and can be acrAB. The preferred inhibitors are as described above.

According to still another aspect of the invention, a method is provided for rendering bacterial cells more susceptible to a non-antibiotic bactericidal or bacteriostatic agent that is a substrate of an efflux pump. The method involves administering to the bacterial cell an inhibitor of the efflux pump. In preferred embodiments the efflux pump is acr-like and can be acrAB. Preferably the inhibitor is selected from the group consisting of about 4% ethanol, methanol, hexane, minocycline and L-phenylalanyl-L-arginyl-β-naphthylamide.

According to another aspect of the invention, a method is provided for modulating (increasing or decreasing) the ability of bacterial cells to survive in an organic solvent. In certain embodiments the method involves enhancing expression in the bacterial cells of an organic solvent bacterial efflux pump by growing the bacterial cells in the presence of a non-mar/sox/rob inducing agent, wherein the agent induces the overexpression of the organic solvent bacterial efflux pump. The agent can be a gene encoding an acr-like pump, the acrAB pump, or expression products thereof. In other embodiments the method involves reducing expression in the bacterial cells of an organic solvent bacterial efflux pump by growing the bacterial cells in the presence of an agent, wherein the agent reduces the expression of the organic solvent bacterial efflux pump. The agent can be an antisense nucleic acid which binds to a gene locus encoding an acr-like pump, especially the acrAB pump, a gene locus which enhances expression of an efflux pump, such as marA, soxA and robA, and the like. The agent also can be a ribozyme or a protein which represses expression of the gene locus. The agent also can be an antibody to an expression product of the foregoing genes. The agent also can be a chemical compound which reduces expression of the efflux pump, or reduces activity of the efflux pump, such as L-phenylalanyl-L-arginyl-β-naphthylamide.

According to another aspect of the invention, a method is provided for testing the ability of a non-antibiotic composition to induce a multiple antibiotic resistance phenotype in a bacterium. The bacterium is contacted with the non-antibiotic composition. The expression of a bacterial gene locus is determined, the altered expression of which is indicative of induction of the multiple antibiotic resistance phenotype in the bacterium. Then, the result of this determination is compared with a control, wherein altered expression of the bacterial gene locus indicates that the non-antibiotic composition induces the multiple antibiotic resistance phenotype in the bacterium. In preferred embodiments, the gene locus is selected from the group consisting of a mar locus, a sox locus, a rob locus and an acr-like efflux pump locus. In one particular embodiment the efflux pump locus is acrAB. The foregoing methods can be carried out using a non-antibiotic composition that is an inactive ingredient. The inactive ingredient can be a non-bactericidal ingredient. The inactive ingredient also can be a non-bacteriostatic ingredient. In one preferred embodiment the method is carried out by determining the enzymatic activity of an expression product of a marker gene, preferably lacZ, fused to the bacterial gene locus.

According to another aspect of the invention, a composition is provided. The composition includes a non-antibiotic bactericidal or bacteriostatic first agent and a second agent that inhibits the expression of activity of an efflux pump. In one embodiment, the second agent inhibits the expression of a gene locus or an expression product thereof, wherein the expression of the gene locus enhances expression of the efflux pump. In preferred embodiments, the second agent is selected from the group consisting of antisense nucleic acids, antibodies, ribozymes and proteins that repress expression of the gene locus. In one preferred embodiment the second agent inhibits an acr-like efflux pump, and particularly preferred is an antisense nucleic acid. The second agent also can be selected from the group consisting of 4% ethanol, methanol, hexane, minocycline and L-phenylalanyl-L-arginyl-β-naphthylamide. The preferred second agent is L-phenylalanyl-L-arginyl-β-naphthylamide. The first agent in some embodiments is selected from the group consisting of triclosan, pine oil, quaternary amine compounds including alkyl dimethyl benzyl ammonium chloride, chloroxylenol, triclocarbon, disinfectants and organic solvents.

According to still another aspect of the invention, a method for identifying an antibacterial composition which does not select for or induce a multiple antibiotic resistance phenotype in a bacterium is provided. The bacterium is contacted with the antibacterial composition. The expression of a bacterial gene locus is determined, the altered expression of which is indicative of induction of the multiple antibiotic resistance phenotype in the bacterium. Then, the result of this determination is compared with a control, wherein altered expression of the bacterial gene locus indicates that the antibacterial composition induces the multiple antibiotic resistance phenotype in the bacterium and a lack of altered expression of the bacterial gene locus indicates that the antibacterial composition does not induce the multiple antibiotic resistance phenotype in the bacterium. In preferred embodiments, the gene locus is selected from the group consisting of a mar locus, a sox locus, a rob locus and an acr-like efflux pump locus. In one particular embodiment the efflux pump locus is acrAB. In one preferred embodiment the method is carried out by determining the enzymatic activity of an expression product of a marker gene, preferably lacZ, fused to the bacterial gene locus.

The invention also provides methods for identifying antibacterials which are not subject to efflux pumps, e.g. those antibacterials which are not substrates for efflux pumps. These antibacterials are those which have bactericidal or bacteriostatic action against bacteria which express an efflux pump, particularly those which overexpress an efflux pump, particularly an acr-like pump, especially acrAB. These and other aspects of the invention are described in greater detail below.

DETAILED DESCRIPTION OF THE INVENTION

Figure 1:
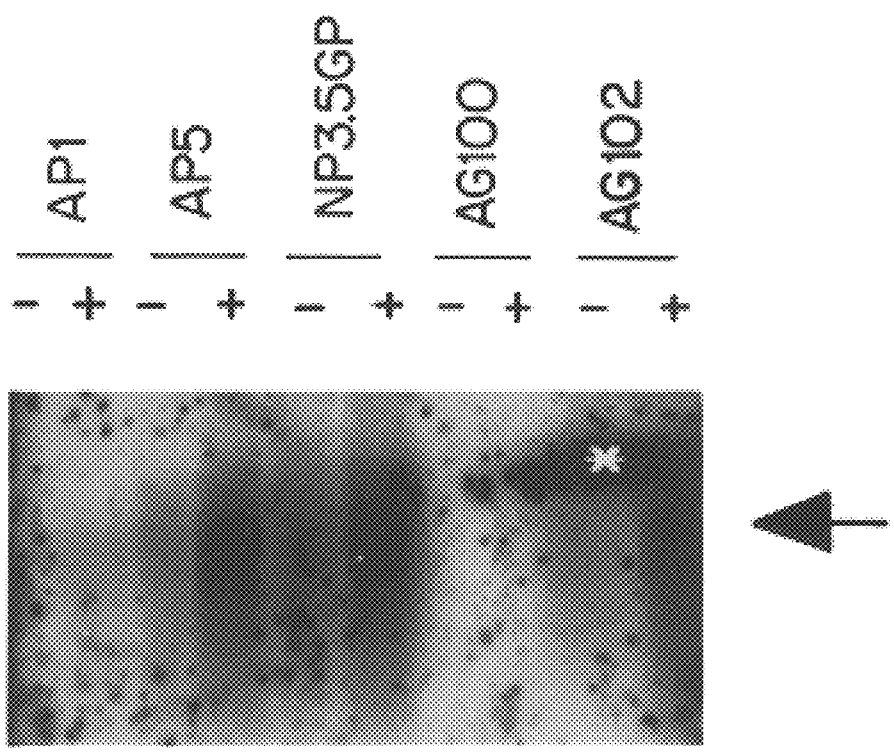
FIG. 1 shows the Northern blot analysis of marRAB mRNA in bacterial mutants.

This invention is based on the discovery that non-antibiotic antibacterial compositions and organic solvents select for mutant bacteria which are resistant not only to the non-antibiotic antibacterial compositions, but also to a range of antibiotics (i.e. a multiple antibiotic resistant phenotype) and also to organic solvents. All of the foregoing compounds are pumped out of bacteria by efflux pumps, i.e., the foregoing compounds are substrates for the efflux pumps. Based on these discoveries it is now possible to enhance the antibacterial properties of non-antibiotic antibacterial compositions and also reduce the selection of bacterial mutants having a multiple antibiotic resistance phenotype by such compositions. The invention also provides methods for testing the ability of non-antibiotic antibacterial compositions to select for or induce a multiple antibiotic resistance phenotype in bacteria. The invention also provides methods for increasing or decreasing bacterial tolerance to organic solvents by increasing or decreasing the activity of bacterial organic solvent efflux pumps, such as by increasing or decreasing expression of an efflux pump, increasing or decreasing expression of genes which positively regulate efflux pump gene loci, and the like. The invention further provides methods for identifying antibacterial compositions which do not select for or induce a multiple antibiotic resistance phenotype in bacteria, such as those antibacterials which are not substrates for efflux pumps. Compositions useful in the foregoing methods are also provided.

As used herein, a non-antibiotic antibacterial composition is a molecule or combination of molecules which are bactericidal or bacteriostatic, but which are not antibiotics. "Antibiotics" are those bactericidal or bacteriostatic compounds which are administered in vivo to people, animals or plants which have a bacterial infection, or which are used in vitro for research on bacterial infections of animals. A non-antibiotic antibacterial composition is not administered to a subject, but rather is used as a disinfectant for killing bacteria or reducing the growth rate of a population of bacteria. Non-antibiotic antibacterial compositions are added as the active ingredients in a variety of industrial and household disinfectants, such as LYSOL™, PINE-SOL™, and the like. Non-antibiotic antibacterial compositions also are added as the antibacterial active ingredient in non-disinfectant compositions such as soaps, lotions, cleansers and the like. More recently, non-antibiotic antibacterial composition have been incorporated into plastics for making a variety of articles of manufacture which have resistance to bacterial growth.

The non-antibiotic antibacterial compositions, as used herein, may have active and inactive ingredients. The active ingredients are, of course, the bactericidal or bacteriostatic agents which have the effect of slowing or stopping growth of populations of bacteria, or even killing such populations of bacteria. Active bactericidal or bacteriostatic ingredients include triclosan, pine oil, quaternary amine compounds such as alkyl dimethyl benzyl ammonium chloride, chloroxylenol, triclocarbon, and other well known disinfectants. The inactive ingredients are the balance of the components of the non-antibiotic antibacterial compositions, including surfactants and other cleansing agents, binders, bulking agents and other compounds. Thus non-antibiotic antibacterial compositions refers both to the active ingredient of the compositions as well as the compositions themselves.

The invention provides methods for inhibiting the selection or propagation of a bacterial mutant that overexpresses an efflux pump. By "inhibiting the selection or propagation", it is meant that the method provides inhibition of selection of a multiple antibiotic resistant bacterial mutant (i.e., the initial mutation event which causes the induction of an efflux pump) and/or inhibition of propagation of a multiple antibiotic resistant bacterial mutant (i.e., growth and/or replication of such bacteria).

The invention also provides methods for rendering bacterial cells more susceptible to non-antibiotic antibacterial compositions by administering to the bacterial cells inhibitors of an efflux pump or a gene locus which enhances expression of the efflux pump, or an expression product thereof. By "administered to", it is meant that the bacterial cells are contacted with the inhibitor for a time sufficient to permit inhibition of the efflux pump or gene locus.

The invention further provides methods for increasing or decreasing organic solvent tolerance of bacterial cells. In these methods, overexpression of an organic solvent efflux pump is induced or decreased by growing the cells in the presence of an agent. By induced "overexpression" it is meant that the organic solvent efflux pump is expressed at a higher level in bacterial cells grown in the presence of an inducing agent than in identical bacterial cells grown under identical conditions but without the agent, i.e., a level of expression that is sufficient to increase organic solvent tolerance. By reduced "expression" it is meant that the organic solvent efflux pump is expressed at a lower level in bacterial cells grown in the presence of an inhibiting agent than in identical bacterial cells grown under identical conditions but without the agent, i.e., a level of expression that is sufficient to reduce tolerance or increase organic solvent susceptibility. These methods can also confer organic solvent tolerance or susceptibility by modulating the activity of an efflux pump as described herein. Organic solvent tolerance or susceptibility can be determined by standard methodologies, including those exemplified in Example 2 below.

One of the features of antibacterial products is the reduction in bacterial populations in those products or on those products, or on surfaces to which such products are applied. As disclosed herein, non-antibiotic antibacterial products also can select for multiple antibiotic resistant bacteria. It would be useful to be able to determine which non-antibiotic antibacterial compositions select for deleterious mutants. Having determined that non-antibiotic antibacterial compositions can select for mutants, it is also possible that other non-antibiotic compositions can select for mutations. Therefore the invention embraces methods for testing the ability of non-antibiotic compositions to induce a multiple antibiotic resistance phenotype. These methods permit testing of any non-antibiotic composition, including the inactive ingredients in cleansers, soaps, disinfectants and the like. In these methods, a bacterial culture is contacted with a non-antibiotic composition and the expression of a gene locus which is indicative of a multiple antibiotic resistant phenotype is determined. The gene locus expression can be determined by any convenient method, of which many are known in the art. These methods include enzyme assays comprising fusions of regulatory loci to a marker gene (e.g. as described for a mar regulatory locus in PCT published application WO94/05810), amplification of gene transcripts (such as using polymerase chain reaction), hybridization methods including Northern blots, and measurement of protein expression including Western blots, ELISA, etc. The level of expression of the gene locus is then compared with a control to determine if the non-antibiotic compositions induced the multiple antibiotic resistant phenotype.

According to the invention, various agents which inhibit the expression or activity of an efflux pump or gene loci which control expression of the efflux pump are useful for reducing selection and/or propagation of mutant bacteria, and also render the cells more susceptible to non-antibiotic antibacterial compositions. These inhibitors are contacted with or administered to the bacterial cells to prevent the undesirable effects of the non-antibiotic antibacterial compositions. One convenient way to ensure contact of the appropriate bacterial cell populations is to include the inhibitors and agents in the non-antibiotic antibacterial compositions. Thus the invention further provides compositions comprising a non-antibiotic bactericidal or bacteriostatic first agent and a second agent which inhibits the expression or activity of an efflux pump, as described above. These compositions can be prepared according to the standard procedures used to prepare non-antibiotic antibacterial compositions. For example, a standard disinfectant composition such as PINE-SOL™ can have added to it an effective amount of an inhibitor of an efflux pump such as described in PCT published patent application WO96/33285, or an antisense nucleic acid which binds to the efflux pump gene locus, etc.

By "effective amount" is meant an amount of the second agent which reduces the selection of mutants by the non-antibiotic first agent. Effective amounts can be determined using standard bacterial growth and mutation assays, including those provided herein. For example, various amounts of the second agent can be added to a non-antibiotic antibacterial composition, and the combined composition can be used as provided in the examples below to select bacterial mutants. Any amount of the second agent which reduces the number of mutants selected relative to the number of mutants selected by the non-antibiotic antibacterial composition alone is an effective amount. One of ordinary skill in the art can determine with no more than routine experimentation what constitutes an effective amount of a second agent, and what amount of a second agent is optimal to prevent selection of mutants by the non-antibiotic antibacterial compositions. Effective amounts of other inhibitors and agents disclosed herein can be determined similarly.

As disclosed herein, inhibitors of the marA gene locus and other loci which regulate efflux pumps are effective to reduce the selection of antibiotic resistant bacterial mutants by non-antibiotic antibacterial compositions, and also potentiate the antibacterial properties of such compositions. The marA gene has been cloned and sequenced, the sequence deposited as GenBank accession number M96235. The marA gene has homologs in *E. coli,* as well as in other species of bacteria. Inhibitors of such marA homologs also are useful for reducing the selection of antibiotic resistant bacterial mutants and potentiating the antibacterial properties of non-antibiotic antibacterial compositions.

For example, the MarA protein is homologous to both SoxS, the effector of the soxRS regulon (Fawcett and Wolf, *Mol. Microbiol.* 14:669–679, 1994; Li and Demple, *J. Biol. Chem.* 269:18371–18377, 1994), and RobA, a small protein that binds to the *E. coli* replication origin and some stress gene promoters (Ariza et al., 1995; Cohen et al., 1995; Jair et al., *J. Bacteriol.* 178:2507–2513, 1996; Skarstad et al., *J. Biol. Chem.* 268:5365–5370, 1993). The soxRS regulon mediates the cell's response to oxidative stress (Amabile-Cuevas and Demple, *Nucleic Acids Res.* 19:4479–4484, 1991; Nunoshiba et al., J. Bacteriol. 174:6054–6060, 1992; Wu and Weiss, *J. Bacteriol.* 173:2864–2871, 1991). soxS genes include those found in S. typhimurium (GenBank accession number U61147) and *E. coli* (GenBank accession numbers X59593 and M60111). robA genes include those found in *E. coli* (GenBank accession numbers AE000509, U00096, M97495 and M94042).

Other known homologs of marA include those found in Enterobacteriaceae by nucleic acid hybridization under stringent conditions (Cohen et al., 1993). Other marA homologs include pqrA, identified in *Proteus vulgaris* (GenBank accession number D13561), ramA identified in *Klebsiella pneumonia* (GenBank accession number U19581), and aarP identified in *Providencia stuartii* (GenBank accession number L38718).

Additional homologs of marA (and other gene loci useful according to the invention) can be identified by conventional techniques. Such techniques include cloning by hybridization to marA or to known homologs thereof, and functional cloning. Cloning by hybridization involves subjecting marA or known homologs thereof to hybridization with nucleic acids of bacteria (preferably the chromosomal DNA) under stringent conditions. The term "stringent conditions" as used herein refers to parameters with which the art is familiar. Nucleic acid hybridization parameters may be found in references which compile such methods, e.g. *Molecular Cloning: A Laboratory Manual,* J. Sambrook, et al., eds., Second Edition, Cold Spring Harbor Laboratory Press, Cold Spring Harbor, N.Y., 1989, or *Current Protocols in Molecular Biology,* F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.15M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1×SDS at temperatures up to 65° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids of the invention. The skilled artisan also is familiar with the methodology for screening cells and libraries for expression of such molecules which then are routinely isolated, followed by isolation of the pertinent nucleic acid molecule and sequencing.

In general homologs typically will share at least 30% nucleotide identity and/or at least 40% amino acid identity to mar/sox/rob genes or to efflux pumps genes, or their polypeptide products respectively, in some instances will share at least 50% nucleotide identity and/or at least 65% amino acid identity and in still other instances will share at least 60% nucleotide identity and/or at least 75% amino acid identity. Watson-Crick complements of the foregoing nucleic acids also are embraced by the invention.

Functional cloning is useful to isolate homologs which do not share sufficient homology at the nucleotide or amino acid sequence level to permit cloning by nucleic acid hybridization, but which nevertheless are functional equivalents of the genes useful in the invention. Functional equivalents need not exhibit the same level of activity, merely activity of the same kind. For example, one phenotypic manifestation of marA expression is the induction of the expression of a set of genes, including acrA. A gene which induces substantially the same set of genes but at a lower level of expression would be considered a functional equivalent.

Functional cloning, as used herein, involves expression of a nucleic acid sequence in a bacterium and determining whether the expression of that sequence confers a desired phenotype on the bacterium. It is known that marA homologs exhibit similar functional characteristics with respect to multiple antibiotic resistance phenotype. For example, overexpression of either soxS or robA in *E. coli* produces both increased organic solvent tolerance and low-level resistance to multiple antimicrobial agents (Ariza et al., *J. Bacteriol.* 177:1665–1661, 1995; Nakajima et al., *Biosci. Biotechnol. Biochem.* 59:1323–1325, 1995a; Nakajima et al., *Appl. Environ. Microbiol.* 61:2302–2307, 1995b). Thus, for marA homologs, the desired phenotype can be multiple antibiotic resistance, induction of mar-regulated genes (see, e.g., U.S. Pat. No. 5,650,321), and the like. For determining multiple antibiotic resistance, all that is necessary is to express the putative marA homolog in a non-multiple antibiotic resistant bacterium and determine whether the modified bacterium acquires resistance to more than one antibiotic, such as tetracycline, chloramphenicol, nalidixic acid, etc. marA homologs can be expressed according to standard procedures, such as transformation with an expression plasmid containing the marA homolog, introduction of one or more copies of the marA homolog on the bacterial chromosome via transposon-mediated insertion, etc.

The acrAB locus, positively regulated by MarA (Ma et al., *Mol. Microbiol.* 16:45–55, 1995) and SoxS and RobA (Ma et al., *Mol. Microbiol.* 19:101–112, 1996), specifies a proton-motive-force-dependent multidrug efflux pump for a wide variety of mostly lipophilic substances (Ma et al., 1995; Nikaido, *Bacteriol.* 178:5853–5859, 1996; Nikaido, *Science* 264:382–387, 1994; Paulsen et al., *Microbiol. Rev.* 60:575–608, 1996). Mar mutants and wild type strains deleted of this locus become equally hypersusceptible to antibiotics (Okusu et al., *J. Bacteriol.* 178:306–308, 1996) suggesting that the acrAB pump confers an intrinsic resistance level which is then enhanced in Mar mutants.

The acrA and acrB genes have been cloned and sequenced. For example, the sequences of acrAB in *E. coli* are deposited as GenBank accession number U00734. The acrAB genes have homologs in *E. coli*, as well as in other species of bacteria. Sequence homologs of acrAB efflux pumps are referred to herein as "acr-like" efflux pumps. Isolation of acr-like efflux pumps and other efflux pumps can be carried out according to the methods described above for nucleic acid hybridization and functional cloning. Inhibitors of such acrAB homologs also are useful for reducing the selection of antibiotic resistant bacterial mutants and potentiating the antibacterial properties of non-antibiotic antibacterial compositions.

Agents which induce overexpression of acr-like efflux pumps are useful in promoting organic solvent tolerance. Inducers of efflux pumps include genes which encode the various efflux pumps which when expressed in a bacterium as a nucleic acid operably linked to a promoter can increase the numbers of efflux pump protein molecules in the bacterium. Agents also include molecules which inhibit the function of efflux pump regulatory genes. For example, antisense nucleic acids which bind to acrR and prevent its transcription or translation would function as inducers of acrAB. Efflux pumps can also be induced by mutation of regulatory genes (such as acrR for the acrAB pump).

Agents useful in decreasing the expression or activity of an efflux pump for increasing organic solvent susceptibility (decreasing organic solvent tolerance) are provided in the following paragraphs.

Agents which bind to a gene locus which mediates enhanced expression of an efflux pump (such as the mar/sox/rob class of genes) or a nucleic acid expression product thereof include antisense nucleic acids, ribozymes and regulatory proteins such as repressor proteins (e.g. MarR). For example, antisense nucleic acids which bind to marA and prevent transcription or translation thereof would function as inhibitors of marA and agents which bind marA. Agents which bind to a protein expression product of a gene locus include antibodies. Inhibitors of the foregoing gene loci and expression products also include molecules which bind to the gene loci and expression products as described above. Other classes of agents and inhibitors of these types will be known to those of skill in the art.

Classes of inhibitors of efflux pumps useful in the methods and compositions of the invention have been described previously in PCT published patent application WO96/33285 (including L-phenylalanyl-L-arginyl-β-naphthylamide). Methods for testing compounds for efflux pump inhibition are also described therein. Other useful inhibitors include ethanol (concentrations of about 4%), methanol, hexane and minocycline. Still other inhibitors include antisense nucleic acids and ribozymes directed against the gene(s) encoding the efflux pump. For example, antisense nucleic acids which bind to acrAB genes and prevent transcription or translation thereof would function as inhibitors of acrAB. Antibodies which bind efflux pumps or proteins which regulate the expression of efflux pumps are another class of inhibitors. Still other inhibitors include genes which repress expression of the efflux pumps or regulatory loci (such as marR) which regulate expression of efflux pumps. Increasing the amount of such genes or the expression products thereof reduces the expression of efflux pumps in bacteria.

As mentioned above, the invention embraces antisense nucleic acids, including oligonucleotides, that selectively bind to a nucleic acid molecule encoding an efflux pump (e.g. acrA) or a molecule which regulates expression of an efflux pump (e.g. marA). As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an RNA transcript of that gene and, thereby, inhibits the transcription of that gene and/or the translation of that RNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon the nucleic acid sequence of a gene of interest, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., Nature Biotechnol. 14:840–844, 1996). Most preferably, the antisense oligonucleotides comprise a complementary sequence of 20–30 bases. Although oligonucleotides may be chosen which are antisense to any region of the gene or RNA transcripts, in preferred embodiments the antisense oligonucleotides correspond to N-terminal or 5' upstream sites such as translation initiation, transcription initiation or promoter sites. In addition, 3'-untranslated regions may be targeted. In addition, the antisense is targeted, preferably, to sites in which RNA secondary structure is not expected and at which proteins are not expected to bind.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by standard methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates preparations containing modified antisense molecules that are complementary to and hybridizable with, under physiological conditions, nucleic acids encoding mar/sox/rob or efflux pump polypeptides, together with one or more carriers.

As described above, the invention further embraces the use of antibodies or fragments of antibodies having the ability to selectively bind to efflux pumps, as well as polypeptides which regulate the expression of efflux pumps. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation. Any of the foregoing antigen fragments are useful in the methods and compositions of the invention. The present invention also includes so-called single chain antibodies and intracellular antibodies.

EXAMPLES

Example 1

Mutants resistant to Pine-Sol/pine oil were obtained from stationary phase LB broth cultures of *E. coli* strain "WEC"

(wild type strain 15-5068 from Carolina Biological Supply Co., Burlington, N.C.) and AG100 (George and Levy, *J. Bacteriol.* 155:531–540, 1983), at 30° C. on nutrient agar (NP 3.5GP) or LB agar with 2–3 days incubation in a variety of ways: using a 6 mm disc method; plating cells on plates or gradient plates (Curiale and Levy, *J. Bacteriol.* 151:209–215, 1982), containing PINE-SOL™ (product of Clorox Co., Oakland, Calif.) or pine oil itself.

Antibiotic susceptibility was measured at 30° C. using antibiotic susceptibility discs (Carolina Biological), gradient plates with the drug in the top agar (Curiale and Levy, 1982) or agar dilution plates (concentration steps of 1.5 fold; inocula of $10^5$ cells/5 µl spot). While there was a variability of resistance phenotypes, all Pine-Sol/pine oil-selected mutants were also multidrug resistant (Table 1 A, B).

TABLE 1

Susceptibility of Pine-Sol/pine oil and Mar mutants to Pine-Sol and to antibiotics[a]

Table 1A

| Strain | Characteristics | Susceptibility by discs; diameter of clearing (mm) | | |
|---|---|---|---|---|
| | | Ap | Cm | Tc |
| WEC | wild type | 22 | 27 | 21 |
| NP3.5GP | mutant of WEC selected on Pine-Sol gradient (0–1.5%) | 12 | 11 | 14 | mutant, caused a Mar phenotype (Cohen et al., *J. Bacteriol.* 175:1484–1492, 1993). These Mar mutants, as well as AG102 were resistant to Pine-Sol (Table 1B) and to 100% pine oil when compared to their respective wild type strains.

TABLE 2

Effect of inactivation of mar, sox, rob, or acr locus upon susceptibility to Pine-Sol

| Strain | Relative MIC for Pine-Sol[a] | | | |
|---|---|---|---|---|
| | mar[b] | sox[b] | rob[b] | acr[b] |
| AG100 | 1 | 0.9 | 0.8 | <0.06 |
| AP1 | 0.5 | <0.6 | 0.5 | <0.02 |
| AP5 | 0.4 | 0.9 | 0.8 | <0.02 |
| APS3 | 0.4 | 1 | 1 | <0.04 |
| AG102 | 0.4 | 1 | 1 | <0.03 |

[a]Relative MIC is the MIC of the inactivated strain divided by the MIC of the strain before inactivation. Values in bold face indicate notable increases in susceptibility. Values obtained from both gradient plate and agar dilution experiments were averaged.
[b]Inactivated locus Northern blot analysis for expression of marA mRNA using a [radiolabeled] marA probe in the absence and presence of the inducer salicylate (Cohen et al., *J. Bacteriol.* 175:7856–7862, 1993) revealed that, like Mar mutant AG102, mutants AP5 and NP3.5GP showed an over expression of marA that was enhanced by salicylate (FIG. 1). Over expression was also seen in mutant APS3 (data not shown). The wild type AG100 and the pine oil mutant AP1 showed

TABLE 1B

| Strain | Characteristics | Susceptibility by gradient plates (MIC)[b] | | | | |
|---|---|---|---|---|---|---|
| | | (% by volume) | (µg/ml) | | | |
| | | PS | Ap | Cm | Nal | Tc |
| AG100 | wild type | 0.9 | <1.2 | 2.6 | 1.7 | 1.8 |
| AP1 | mutant of AG100 selected by pine oil on disc | >3.6/0.9 | 3.0 | 7.8 | 9.7 | 2.4 |
| AP5 | mutant of AG100 selected as for AP1 | >2.9/0.9 | 7.2 | 21 | 7.5 | 4.5 |
| APS3 | mutant of AG100 selected on Pine-Sol gradient (0–1.5%) | 1.8 | 7.7 | >35 | 8.6 | 5.3 |
| AG102 [1][d] | Mar mutant of AG100, selected on Tc (2 steps) | >4.1 | 8.5 | >35 | 14.0 | >12.8 |
| HH180 [2][d] | deletion of 39 kb including mar locus; has zdd-230::Tn9 (Cm$^R$); in host strain MM294 | 0.3 | <0.6 | ND$^C$ | <1.8 | <0.6 |
| HH188 [2][d] | HH180 containing pHHM183 (mar+) | 0.9 | <1.0 | ND$^C$ | 3.7 | 1.2 |
| HH191 [2][d] | HH180 containing pHHM191 (marR2) | 2.3 | 5.4 | ND$^C$ | 9.1 | 8.2 |
| HH193 [2][d] | HH180 containing pHHM193 (marR5) [3][d] | 3.2 | 5.9 | ND$^C$ | 10.9 | >11.4 |

[a]Abbreviations: PS (Pine-Sol), Ap (ampicillin), Cm (chloramphenicol), Nal (nalidixic acid), Tc (tetracycline).
[b]Gradient plate values were the averages of two to four experiments, except in the case of chloramphenicol, which involved a single determination.
[c]Host strain is CmR due to Tn9, so values were not determined (ND).
[d]References: 1) George et al., 1983; 2) Cohen et al., 1993; 3) Seoane and Levy, 1995

In host strain HH180, deleted of the entire mar region, plasmid pHHM188, bearing a 9 kb wild type mar caused no change in the resistance phenotype. In the same host pHHM191 and pHHM193 each containing cloned 9 kb fragment including the entire mar locus, and marR was no detectable signal (FIG. 1). We concluded that AP5, NP3.5GP, and APS3, but not AP1, were probably Mar mutants.

The marCORAB locus was deleted in the Pine-Sol/pine oil mutants and in AG102 by P1 transduction (Provence and Curtiss, p. 317–347, In Gerhardt et al., eds., *Methods for General and Molecular Bacteriology*. ASM, Washington, D.C., 1994) using AG100/Kan (Maneewannakul and Levy, 1996) as the donor strain and selecting on kanamycin. The deletion caused a 60–70% reduction in the resistance of mutants to Pine-Sol (Table 2), down to approximately a wild type level. The same was true for mutant NP3.5GP (data not shown).

Inactivation of the soxRS and robA loci in the Pine-Sol/pine oil and Mar mutants via P1 transduction of a kanR gene in the gene caused decreased resistance to Pine-Sol only in the mutant AP1 (Table 2). Mutant AP1 did not overexpress mar or soxRS (data not shown). Deletion of the acrAB locus by P1 transduction of kanR in the gene increased susceptibility to Pine-Sol in all strains (Table 2).

Deletion of acrAB (but not of mar) also caused more than a ten fold increase in the susceptibility of strains to the products containing the quaternary amine or chloroxylenol (data not shown), suggesting that AcrAB was also involved in effluxing those two disinfectants.

Example 2

Organic solvent tolerance mediated by the marA, soxS, robA and acrAB loci of *E. coli* is described in White et al. (*J. Bacteriol.* 179:6122–6126, 1997). These results are summarized below. AG102, a Mar mutant of AG100, grew in the presence of n-hexane, cyclohexane (Table 3), and n-pentane (data not shown) whereas AG100 grew only in hexane.

TABLE 3

Organic solvent tolerance of wild-type and mar strains bearing mar, soxS, or robA plasmids.

| Strain | Plasmid[b] | Growth in presence of organic solvent[a] | |
|---|---|---|---|
| | | n-hexane (3.9)[c] | cyclohexane (3.4) |
| AG 102 (marR mutation) | | ++ | ++ |
| AG100 (wild-type) | | ++ | − |
| AG100 | pMAK-TU1 | ++ | − |
| AG100 | pMAK-TU2 | ++ | + |
| AG100 | pMAK-TU1 & TU2 | ++ | ++ |
| AG100 | pSMarAB | ++ | + |
| AG100 | pSXS | ++ | ++ |
| AG100 | pSRob | ++ | ++ |
| AG100K (marCORAB::kan) | | + | − |
| AG100K | pMAK-TU1 | + | − |
| AG100K | pMAK-TU2 | ++ | + |
| AG100K | pMAK-TU1 & TU2 | ++ | ++ |
| AG100K | pSMarAB | ++ | + |
| AG100K | pSXS | ++ | ++ |
| AG100K | pSRob | ++ | ++ |
| MCH164 (Δmar) | | + | − |
| MCH164 | pMAK-TU1 | + | − |
| MCH164 | pMAK-TU2 | ++ | − |
| MCH164 | pMAK-TU1 & TU2 | ++ | ++ |
| MCH164 | pSMarAB | ++ | − |
| MCH164 | pSXS | ++ | − |
| MCH164 | pSRob | ++ | − |
| AG100-B (acrR mutant) | | ++ | + |
| AG100-A (ΔacrAB) | | − | − |
| AG102-A (marR1, ΔacrAB) | | − | − |
| AG102-A | pSMarAB | − | − |
| AG102-A | pSXS | − | − |
| AG102-A | pSRob | − | − |

[a](++) signifies confluent growth; (+) visible growth (≦100 colonies); (−) signifies no growth.
[b]IPTG was added to plates at a concentration of 0.5 mM when induction of plasmid genes was required (pSE380 derivatives).
[c]Values in parentheses are log Pow.

In the wild type *E. coli* AG100 background, over expression of marA (on plasmid pSMarAB or pMAK-TU2) or soxS (on pSXS) or robA (on pSRob) resulted in cyclohexane tolerance (Table 3). marC by itself (pMAK-TU1) had no effect on cyclohexane tolerance, however, introduction of marCORAB on the low copy plasmid pMAK705 (pMAK-TU1&TU2) resulted in cyclohexane tolerance (Table 3).

When the mar locus was inactivated by replacement with a kanamycin resistance cassette (AG100K) (Maneewannakul and Levy, 1996), the strain became hypersusceptible to n-hexane as compared to the wild type strain (Table 3). MCH164 [a derivative of AG100 from which 39 kb of chromosomal DNA including the entire mar locus had been deleted (Goldman et al., *Antimicrob. Agents-*

Chemother. 40:1266–1269, 1996; McMurry et al., *Antimicrob. Agents Chemother.* 38:542–546, 1994)] was, as expected, also hypersusceptible to organic solvents (Table 3). Expression in trans of marA, soxS, or robA in AG100K, restored n-hexane tolerance, and increased cyclohexane tolerance in the cell (Table 3). Expression in trans in AG100K of marA, specified from plasmid pMAK-TU1&TU2 restored n-hexane tolerance and produced higher cyclohexane tolerance (Table 3). While introduction of either marA, soxS, or robA restored n-hexane tolerance in MCH164, only pMAK-TU1&TU2 produced cyclohexane tolerance in this larger deletion mutant (Table 3).

Overexpression of acrAB, because of a mutation in acrR in AG100-B, enabled the strain to grow in the presence of cyclohexane (Table 3). Deletion of acrAB from wild-type AG100 (AG100-A) resulted in n-hexane sensitivity (Table 3). Deletion of acrAB from the Mar mutant (AG102-A) resulted in both n-hexane and cyclohexane sensitivity. Expression of marA, soxS, or robA in AG102-A failed to restore organic solvent tolerance, further demonstrating the critical role of acrAB (Table 3).

*E. coli* strains overexpressing MarA (JHC1069; cfxB1/MarR mutation) or SoxS (JTG1078; soxR105 mutation) grew in the presence of both n-hexane and cyclohexane, whereas the wild-type C4468 only grew in the presence of n-hexane (Table 4). Much like the situation in AG100, introduction of either pSMarAB, pMAK-TU2, pMAK-TU1&TU2, pSXS, or pSRob into GC4468 produced cyclohexane tolerance. Inactivation of robA by insertion of a kanamycin cassette (RA4468) caused n-hexane susceptibility (Table 4). Introduction of either marA (on pMAK-TU1&TU2, pMAK-TU2, or pSMarAB), SoxS (on pSXS), or RobA (on pSRob), into the robA inactivated strain, increased both n-hexane and cyclohexane tolerance (Table 4). Deletion of soxRS (DJ901) had little effect on n-hexane tolerance (Table 4). Introduction of marA, soxS, or robA into the ΔsoxRS strain produced cyclohexane tolerance (Table 4). In all these complementations, the effect of marA was best noted from plasmid pMAK-TU1&TU2.

TABLE 4

Organic solvent tolerance of wild-type, ΔsoxRS, or robA::Kan strains bearing mar, soxS, or robA plasmids.

| | | Growth in presence of organic solvent[a] | |
|---|---|---|---|
| Strain | Plasmid[b] | n-hexane (3.9)[c] | cyclohexane (3.4) |
| GC4468 (wild-type) | | ++ | − |
| JHC1069 (cfxB1) | | ++ | ++ |
| JTG1078 (soxR105) | | ++ | ++ |
| GC4468 | pMAK-TU1 | ++ | − |
| GC4468 | pMAK-TU2 | ++ | + |
| GC4468 | pMAK-TU1 & TU2 | ++ | ++ |
| GC4468 | pSMarAB | ++ | + |
| GC4468 | pSXS | ++ | ++ |
| GC4468 | pSRob | ++ | ++ |
| RA4468 (robA::kan) | | + | − |
| RA4468 | pMAK-TU1 | + | − |
| RA4468 | pMAK-TU2 | ++ | + |
| RA4468 | pMAK-TU1 & TU2 | ++ | ++ |
| RA4468 | pSMarAB | ++ | + |
| RA4468 | pSXS | ++ | ++ |
| RA4468 | pSRob | ++ | ++ |
| DJ901 (ΔsoxRS) | | ++ | − |
| DJ901 | pMAK-TU1 | ++ | − |
| DJ901 | pMAK-TU2 | ++ | + |
| DJ901 | pMAK-TU1 & TU2 | ++ | ++ |
| DJ901 | pSMarAB | ++ | + |
| DJ901 | pSXS | ++ | ++ |
| DJ901 | pSRob | ++ | ++ |

[a](++) signifies confluent growth; (+) visible growth (≦100 colonies); (−) signifies no growth.
[b]IPTG was added to plates at a concentration of 0.5 mM when induction of plasmid genes was required (pSE380 derivatives).
[c]Values in parenthese are log Pow.

These results show that overexpression of marA, soxS, or robA leads to increased organic solvent tolerance and that tolerance is mediated by the acrAB efflux pump.

Equivalents

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference.

We claim:

1. A method for screening the ability of an organic solvent to induce a multiple antibiotic resistance (Mar) phenotype in a microbe comprising:
   (a) contacting the microbe with a composition comprising an organic solvent,
   (b) determining the expression of an acr-like efflux pump gene locus, and
   (c) comparing the result of (b) with a control, wherein altered expression of the acr-like efflux pump gene locus indicates that the composition induces the multiple antibiotic resistance phenotype in the microbe.

2. The method of claim 1, wherein the efflux pump locus is an acrAB locus.

3. The method of 1, wherein the organic solvent is selected from the group consisting of: n-hexane, cyclohexane, and n-pentane.

4. The method of claim 1, wherein step (b) is performed by determining the level of expression of a product produced from a marker gene fused to the microbial acr-like efflux pump gene locus.

5. The method of claim 4, wherein the marker gene is lacZ.

6. The method of claim 4, wherein he efflux pump locus is an acrAB locus.

* * * * *

UNITED STATES PATENT AND TRADEMARK OFFICE
CERTIFICATE OF CORRECTION

PATENT NO. : 6,068,972
DATED : May 30, 2000
INVENTOR(S) : Stuart B. Levy

It is certified that error appears in the above-identified patent and that said Letters Patent is hereby corrected as shown below:

Last page, Claim 6 please delete

"he" and insert --the--

Signed and Sealed this

Twenty-second Day of May, 2001

Attest:

NICHOLAS P. GODICI

*Attesting Officer*                *Acting Director of the United States Patent and Trademark Office*